(12) United States Patent
Souda

(10) Patent No.: US 8,263,779 B2
(45) Date of Patent: Sep. 11, 2012

(54) METHOD FOR SEPARATING AND PURIFYING α-UNSATURATED AMINE COMPOUND

(75) Inventor: Hiroshi Souda, Oita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 308 days.

(21) Appl. No.: 12/672,209

(22) PCT Filed: Aug. 8, 2008

(86) PCT No.: PCT/JP2008/064293
§ 371 (c)(1),
(2), (4) Date: Feb. 4, 2010

(87) PCT Pub. No.: WO2009/020203
PCT Pub. Date: Feb. 12, 2009

(65) Prior Publication Data
US 2011/0184184 A1    Jul. 28, 2011

(30) Foreign Application Priority Data

Aug. 8, 2007   (JP) ................................. 2007-206350

(51) Int. Cl.
C07D 213/61    (2006.01)
(52) U.S. Cl. ...................................................... 546/332
(58) Field of Classification Search ............... 546/332
See application file for complete search history.

(56) References Cited

U.S. PATENT DOCUMENTS

| 5,364,989 A | 11/1994 | Aoki et al. |
| 5,849,768 A | 12/1998 | Minamida et al. |

FOREIGN PATENT DOCUMENTS

| EP | 00529680 A2 | 3/1993 |
| GB | 2 228 003 A | 8/1990 |
| JP | 2-000171 A | 1/1990 |
| JP | 2-275841 A | 11/1990 |
| JP | 3048370 A | 11/1990 |
| JP | 7-224036 A | 8/1995 |
| JP | 2551392 A | 8/1995 |
| JP | 2551393 A | 8/1995 |

OTHER PUBLICATIONS

Stephenson, R. M. J. Chem. End. Data. 1993, 38, 428-431.*
Armarego et al. Purification of Laboratory Chemicals, 4th edition, 1996, p. 27.*
International Preliminary Report on Patentability for corresponding International Patent Application No. PCT/JP2008/064293 mailed Mar. 4, 2010.
Isao Minamida, et al., "Synthesis and Insecticidal Activity of Acyclic Nitroethene Compounds Containing a Heteroarylmethylamino Group", J. Pesticide Sci., vol. 18, No. 1, Feb. 20, 1993, pp. 41-48.
Isao Minamida, et al., "Synthesis and Insecticidal Activity of Acyclic Nitroethene Compounds Containing a 3-Pyridylmethylamino Group", J. Pesticide Sci., vol. 18, No. 1, Feb. 20, 1993, pp. 31-40.
The State Intellectual Property Office of the People's Republic of China, "Second Office Action," issued in connection with Chinese Patent Application No. 200880102298.x, dated Jun. 19, 2012.

* cited by examiner

*Primary Examiner* — Joseph Kosack
*Assistant Examiner* — Matthew Coughlin
(74) *Attorney, Agent, or Firm* — Sughrue Mion, PLLC

(57) ABSTRACT

A method for purifying an α-unsaturated amine compound represented by Formula (1), the method comprising a step of extracting with water the compound of Formula (1) from a crude product of the α-unsaturated amine compound represented by Formula (1), and a step of extracting with a pyridine solvent the α-unsaturated amine compound of Formula (1) from the aqueous solution containing the compound of Formula (1) obtained in the previous step to obtain a pyridine solvent solution of the compound of Formula (1):

[Chemical Formula 1]

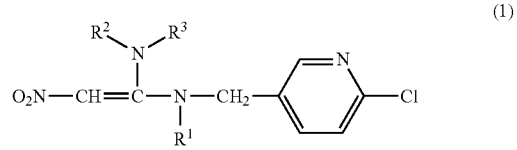

(1)

wherein $R^1$ represents a hydrogen atom, a $C_{1-4}$ alkyl group, a halo $C_{1-4}$ alkyl group, a $C_{1-4}$ alkoxy-$C_{1-4}$ alkyl group, a $C_{7-9}$ aralkyl group, or an optionally substituted phenyl group, $R^2$ represents a hydrogen atom, a $C_{1-4}$ alkyl group, or a $C_{7-9}$ aralkyl group, and $R^3$ represents a hydrogen atom, a $C_{1-5}$ alkyl group, a halo $C_{1-4}$ alkyl group, a hydroxy $C_{1-4}$ alkyl group, a $C_{1-4}$ alkoxy-$C_{1-4}$ alkyl group, $C_{2-4}$ alkenyl group, or a $C_{7-9}$ aralkyl group.

4 Claims, No Drawings

METHOD FOR SEPARATING AND PURIFYING α-UNSATURATED AMINE COMPOUND

TECHNICAL FIELD

The present invention relates to a method for separating and purifying an α-unsaturated amine compound effective as an agricultural chemical ingredient for its insecticidal and miticidal activities.

BACKGROUND ART

The α-unsaturated amine compound is a compound effective as an ingredient of agricultural chemicals, and Patent Document 1, for example, describes the insecticidal activities of the compound.

Organic synthesis procedures for synthesizing an α-unsaturated amine compound often generate by-products and leave raw material compounds. For example, Patent Document 2 discloses a method for separating and purifying an α-unsaturated amine compound by concentrating a reaction mixture containing the α-unsaturated amine compound followed by a silica gel column chromatography, but the method can hardly be said to be suitable for industrial-scale production. Patent Document 3 describes a separation and purification method comprising separating a reaction mass, extracting an α-unsaturated amine compound with chloroform, and adding ethyl acetate to the compound to crystallize it. However, chlorinated organic solvents such as chloroform raise concerns about hazardous effects on human body and environment. It is hard to say that the conventional methods are always satisfactory separating and purifying methods because they are not suitable for industrial-scale production or not sensitive enough to environmental issues.

Patent Document 1: Japanese Patent No. 2551392
Patent Document 2: Japanese Patent No. 2551393
Patent Document 3: Japanese Patent No. 3048370

DISCLOSURE OF THE INVENTION

Problems to be Solved by the Invention

One of the factors that made such a procedure indispensable for separating and purifying an α-unsaturated amine compound is that the α-unsaturated amine compound is highly soluble in water and has extremely low solubility in common organic solvents, resulting in that sufficient extraction efficiency cannot be attained with any solvents other than chlorinated organic solvents.

The present inventors conducted extensive studies to solve the problems described above, and found a method for separating and purifying an α-unsaturated amine compound suitable for industrial-scale production by using a pyridine derivative as a solvent and has achieved the present invention.

Means for Solving the Problems

More specifically, the present invention is to provide a method for purifying an α-unsaturated amine compound represented by Formula (1), comprising a step of extracting with water the compound of Formula (1) from a crude product of the α-unsaturated amine compound represented by Formula (1), and a step of extracting with a pyridine solvent the α-unsaturated amine compound of Formula (1) from the aqueous solution containing the compound of Formula (1) obtained in the previous step to obtain a pyridine solvent solution of the compound of Formula (1):

[Chemical Formula 1]

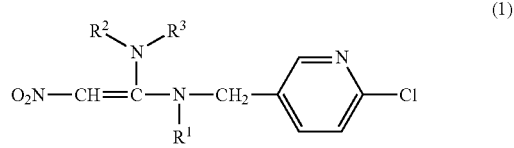

wherein $R^1$ represents a hydrogen atom, a $C_{1-4}$ alkyl group, a halo $C_{1-4}$ alkyl group, a $C_{1-4}$ alkoxy-$C_{1-4}$ alkyl group, a $C_{7-9}$ aralkyl group, or an optionally substituted phenyl group, $R^2$ represents a hydrogen atom, a $C_{1-4}$ alkyl group, or a $C_{7-9}$ aralkyl group, and $R^3$ represents a hydrogen atom, a $C_{1-5}$ alkyl group, a halo $C_{1-4}$ alkyl group, a hydroxy $C_{1-4}$ alkyl group, a $C_{1-4}$ alkoxy-$C_{1-4}$ alkyl group, $C_{2-4}$ alkenyl group, or a $C_{7-9}$ aralkyl group.

Effect of the Invention

According to the production method of the present invention, the α-unsaturated amine compound effective as an active ingredient of an insecticide and represented by Formula (1) can be separated and purified by a method which does not require a chlorine-based solvent and is yet suitable for industrial-scale production.

BEST MODE FOR CARRYING OUT THE INVENTION

Hereinafter, the present invention is described. Examples of the $C_{1-4}$ alkyl group represented by $R^1$ in the Formula 1 include a methyl group, an ethyl group, an n-propyl group, an i-propyl group, an n-butyl group, an i-butyl group, an s-butyl group, and a t-butyl group.

Examples of the halo $C_{1-4}$ alkyl include $C_{1-4}$ alkyl groups substituted with fluorine, chlorine or bromine such as a monochloromethyl group, a dichloromethyl group, a trichloromethyl group, a monofluoromethyl group, a difluoromethyl group, a trifluoromethyl group, a 2-chloroethyl group, a 2,2,2-trichloroethyl group, a 2-fluoroethyl group, a 2,2,2-trifluoroethyl group, and a 1,1,2,2-tetrafluoroethyl group.

Examples of the $C_{1-4}$ alkoxy-$C_{1-4}$ alkyl group include a methoxymethyl group, an ethoxymethyl group, a 1- or 2-methoxyethyl group, and a 3-methoxypropyl group. Examples of the $C_{7-9}$ aralkyl include a benzyl group, a 4-methylbenzyl group, a phenethyl group, and a 4-methylphenethyl group.

Examples of the optionally substituted phenyl group include a phenyl group, or phenyl groups substituted with 1 to 4 substituents selected from a halogen atom (fluorine, chlorine, bromine or iodine), a $C_{1-3}$ alkyl group (methyl group, ethyl group, propyl group, and the like), a $C_{1-3}$ alkoxy (methoxy group, ethoxy group, propoxy group, and the like), an amino group, a hydroxy group, and a carboxy group.

Examples of the $C_{1-4}$ alkyl group and $C_{7-9}$ aralkyl group represented by $R^2$ in Formula (1) include the same as those described for $R^1$.

Examples of the $C_{1-5}$ alkyl group represented by $R^3$ in Formula (1) include an amyl group in addition to the $C_{1-4}$ alkyl groups listed for $R^1$. Examples of the halo $C_{1-4}$ alkyl group, $C_{1-4}$ alkoxy-$C_{1-4}$ alkyl group and $C_{7-9}$ aralkyl group include the same as those listed for $R^1$. Examples of the hydroxy $C_{1-4}$ alkyl group include a hydroxy methyl group, a 1- or 2-hydroxy ethyl group and a 3-hydroxy propyl group. Examples of the $C_{2-4}$ alkenyl group include a vinyl group, an allyl group and an isopropenyl group.

In the method of the present invention, a compound is preferably that $R^1$ represents a hydrogen atom, a $C_{1-4}$ alkyl group or a halo $C_{1-4}$ alkyl group, $R^2$ represents a hydrogen atom or a $C_{1-4}$ alkyl group, and $R^3$ is a hydrogen atom, a $C_{1-4}$ alkyl group or a halo $C_{1-4}$ alkyl group in Formula (1), and more preferably that $R^1$ and $R^2$ represent a $C_{1-4}$ alkyl group, and $R^3$ represents a hydrogen atom.

The crude product of the α-unsaturated amine compound of Formula (1) is typically obtained by the method shown in Scheme (I) below as described in Patent Document 3.

[Chemical Formula 2]

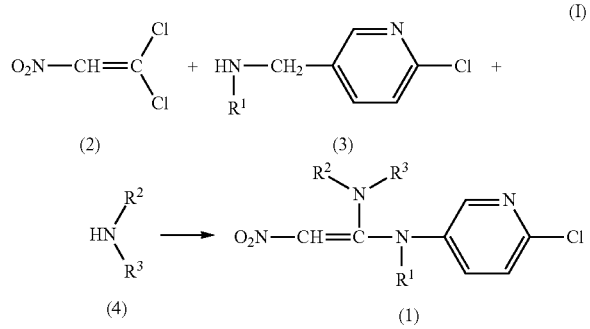

In the reaction shown in the Scheme (I), 1,1-dichloro-2-nitroethene represented by Formula (2) may be reacted first with the pyridyl methyl amine compound of Formula (3), or may be reacted first with the amine compound of Formula (4). More specifically, the crude product of the α-unsaturated amine compound of Formula (1) is typically obtained by reacting 1,1-dichloro-2-nitroethene represented by the Formula (2) with the pyridyl methyl amine compound represented by the Formula (3) and subsequently reacting the obtained product with the amine compound represented by the Formula (4); or by reacting the 1,1-dichloro-2-nitroethene represented by the Formula (2) with the amine compound represented by the Formula (4) and subsequently reacting the obtained product with the pyridyl methyl amine compound represented by the Formula (3). The sequence of reaction of the pyridyl methyl amine compound (3) and the amine compound (4) can be any, but, in the case of a primary amine and secondary amine combination, it is preferable to react a secondary amine first.

The reaction is preferably carried out in an organic solvent.

Examples of the usable organic solvent include aliphatic hydrocarbons such as hexane, heptane, petroleum ether, ligroin, and cyclohexane; aromatic hydrocarbons such as benzene, toluene, xylene, and chlorobenzene; alcohols such as isopropanol, and tert-butanol; ethers such as diethyl ether, diisopropyl ether, and 2-methyltetrahydrofuran; ketones such as di-n-butyl ketone; nitriles such as propionitrile and benzonitrile; and esters such as methyl acetate, ethyl acetate, and n-butyl acetate. Esters such as ethyl acetate and n-butyl acetate are preferable.

The reaction is preferably carried out in the presence of a base. Examples of the base include organic bases such as triethylamine, tri-n-propylamine, pyridine, collidine, quinoline, dimethylaniline, methyldicyclohexylamine, 1,5-diazabicyclo[4,3,0]non-5-ene, 1,4-diazabicyclo[2,2,2]octane, 1,8-diazabicyclo[5,4,0]-7-undecene, and 3,4-dihydro-2H-pyrid[1,2-a]pyrimidin-2-one; inorganic bases such as sodium hydrogencarbonate, potassium hydrogencarbonate, sodium carbonate, potassium carbonate, sodium hydroxide, potassium hydroxide, and calcium hydroxide; carboxylates such as sodium acetate, and potassium acetate; etc. Inorganic bases such as sodium carbonate, potassium carbonate, sodium hydroxide, and potassium hydroxide are preferable. The amount of the base used is 2 to 5 equivalents, preferably 2 to 3 equivalents, to the compound of the Formula (2). The amine compound of the Formula (4) itself used in the reaction may be used as the base. The timing for adding the base to the reaction system is not limited insofar as the reaction is not hindered.

The reaction may be typically selected from the range of −80 to 120° C., is preferably −40° C. or higher, and particularly appropriately −20 to 50° C. The reaction time is not limited, but the reaction is completed typically from about 5 minutes to about 5 hours.

The crude product obtained by such a reaction typically contains, in addition to the solvent and the α-unsaturated amine compound of Formula (1) used in the reaction, lipophilic by-products (the compound of the Formula (3) or the Formula (5), or the mixture of both compounds) or hydrophilic by-products (the compound of the Formula (4) or the Formula (6), or the mixture of the both compounds). A method for selectively obtaining the intended α-unsaturated amine compound in high purity from such a reaction crude product is, for example, a method including the steps (1), (2) and (3) as shown below.

[Chemical Formula 3]

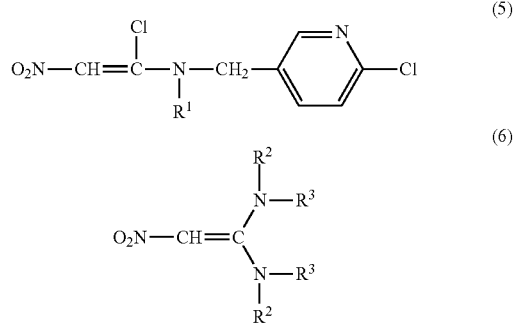

(1) a step of extracting with water an α-unsaturated amine compound and a hydrophilic by-product (the compound of the Formula (4) or the Formula (6), or the mixture of the both compounds) from the crude product of the α-unsaturated amine compound of Formula (1) to remove an lipophilic by-products (the compound of the Formula (3) or the Formula (5), or the mixture of both compounds) into the organic layer;

(2) a step of extracting with a pyridine solvent the α-unsaturated amine compound from the aqueous layer to remove the hydrophilic by-products (the compound of the Formula (4) or the Formula (6), or the mixture of both compounds) into the aqueous layer; and (3) a step of crystallizing the α-unsaturated amine compound from the obtained pyridine solvent layer and filtering to obtain the intended α-unsaturated amine compound, or separating and removing the pyridine solvent by a technique such as distillation, or the like, to obtain the intended α-unsaturated amine compound.

In the step (1), the amount of water used for the extraction is typically 0.5 to 10 times by weight, preferably 1 to 5 times by weight, with respect to the α-unsaturated amine compound of Formula (1).

Examples of the pyridine solvent used in the step (2) include pyridine, 2-acetylpyridine, 2-aminopyridine, 2-bromopyridine, 4-t-butylpyridine, 2,4,6-collidine, 2-cyanopyridine, 4-dimethylamino pyridine, 2-diphenylphosphino-6-methylpyridine, 2,3-dimethylpyridine, 2,4- dimethylpyridine, 2,6-dimethylpyridine, 3,4-dimethylpyridine, 3,5-dimethylpyridine, 2,6-dimethoxypyridine, 2-phenylpyridine, 2-picoline, 2-vinylpyridine, 4-vinylpyridine, 2-ethylpyridine, 4-ethylpyridine, 2,6-diphenylpyridine, 2-(p-tolyl)pyridine, and 5-ethyl-2-methylpyridine. Water-immiscible 2,4,6-collidine, 2,6-dimethylpyridine, 2,6-diphenylpyridine, and 5-ethyl-2-methylpyridine are preferable.

The amount of the pyridine solvent used is 0.5 to 50 times by weight, preferably 1 to 20 times by weight, more preferably 2 to 10 times by weight, with respect to the α-unsaturated amine compound of Formula (1).

The extraction in the steps (1) and (2) is typically carried out at a temperature in the range from −10 to 120° C., and lower than the boiling point of a solvent used, particularly preferably −5 to 60° C. The number of times of extraction is not limited, but the larger number of times the extraction is carried out, the higher the recovery rate of the intended α-unsaturated amine compound. Commonly, the extraction is carried out about 2 to 5 times. The extraction can also be carried out by techniques such as multistage extraction or continuous extraction using a mixer-settler, or the like.

The α-unsaturated amine compound extracted with a pyridine solvent can be separated from the solvent by distilling the pyridine solvent off. When the α-unsaturated amine compound is solid, it can also be separated by crystallization and filtration. Typically, separation by the crystallization and filtration can yield a higher-purity α-unsaturated amine compound.

The crystallization method includes cooling crystallization whereby the solubility of an α-unsaturated amine compound is lowered by decreasing a temperature to precipitate crystals; concentration crystallization whereby the concentration of an α-unsaturated amine compound is made supersaturated by distilling a solvent off; anti-solvent addition crystallization whereby an α-unsaturated amine compound is made supersaturated by adding a solvent in which the solubility of the α-unsaturated amine compound is low to precipitate crystals; and further includes continuous crystallization and batch crystallization. Any of the above methods may be employed. The crystallization may also be carried out by combining any of these methods.

In the crystallization methods described above, a seed crystal may also be added. The timing for adding a seed crystal is preferably at the time when the solubility of the α-unsaturated amine compound reaches the saturate point or a little supersaturate point because the addition at these timings can be effective in preventing the nonuniformity in crystal particle size and deteriorated quality caused by the sudden precipitation from the loss of ultrasupersaturated condition. The amount of a seed crystal to be added is not limited, but preferably 0.01 to 10% by weight, more preferably 0.05 to 2% by weight with respect to the crystalline compound to be finally obtained.

The crystallization temperature is not limited, but typically higher than the melting point and lower than the boiling point of a solvent to be used and can be carried out at a temperature of −40° C. to 180° C., preferably −20° C. to 120° C., and more preferably −10° C. to 60° C.

Examples of the antisolvent used in the antisolvent addition crystallization include aliphatic hydrocarbons such as hexane, petroleum ether, ligroin, and cyclohexane; aromatic hydrocarbons such as benzene, toluene, xylene, and chlorobenzene; alcohols such as isopropanol and tert-butanol; ethers such as diethyl ether, diisopropyl ether, dioxane, and tetrahydrofuran; ketones such as methyl ethyl ketone; nitriles such as acetonitrile and propionitrile; esters such as methyl acetate, ethyl acetate, and butyl acetate. Preferables are aliphatic hydrocarbons such as hexane, heptanes, petroleum ether, ligroin, and cyclohexane.

The filtration of the crystalline slurry of the obtained α-unsaturated amine compound may be carried out by a batch process or continuous process, and any filter typically used in the industry such as centrifuge, filter press, belt filter, or drum filter is applicable. The crystals may also be washed as necessary using a pyridine derivative or the solvent described above.

The α-unsaturated amine compound contained in the filtrate can be recycled for the subsequent crystallization and thereafter. As for the recycling method, the filtrate may be directly added to a crystalline mass or may be added after being concentrated by distilling the solvent. Alternatively, the α-unsaturated amine compound may be extracted with water or other organic solvents and subsequently recycled for the next batch.

The obtained wet cake may be dried after granulation or directly dried. The usable dryers include a solid air dryer, a fluidized-bed dryer, a rotary dryer, or the like.

EXAMPLES

Hereinafter, the present invention is described in further detail with reference to Reference Examples, Examples and Application Examples, but the present invention should not be limited to these examples.

Reference Example 1

Synthesis of 1,1,1-trichloro-2-nitroethane

[Chemical Formula 4]

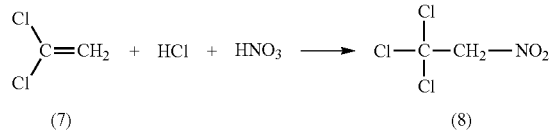

241.6 g of 35% hydrochloric acid was charged in a 500-ml round bottom flask and cooled to 15° C., and then 216.5 g of 69% nitric acid was added dropwise over 1 hour. After stirring the reaction mixture at 15° C. for 2 hours, a vapor phase portion in the reaction container was then replaced with nitrogen, and the $NO_x$ gas generated as a by-product was discharged. The temperature of the reaction mixture was lowered to 10° C., and 173.0 g of 1,1-dichloroethene represented by the above Formula (7) was added dropwise over 3 hours. After stirring the reaction mixture at 10° C. for 2 hours, the reaction mixture was then warmed to 15° C. and the stirring was further continued for 1.5 hours, followed by separating the aqueous layer for removal.

The obtained green organic layer was warmed to 80° C. and stirred for 4 hours, thereby removing the remaining $NO_x$ gas and HCl gas to obtain 304.3 g of a blue solution. The thus obtained solution was analyzed by a gas chromatography, and found to contain 208.5 g of 1,1,1-trichloro-2-nitroethane represented by the above Formula (8). Yield 63.6% (1,1-dichloroethene standard)

Reference Example 2

Synthesis of 1,1-dichloro-2-nitroethene

[Chemical Formula 5]

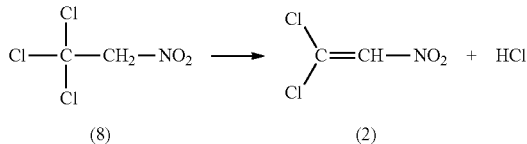

245.7 g of the 1,1,1-trichloro-2-nitroethane solution (1,1,1-trichloro-2-nitroethane net weight 168.3 g) obtained in Reference Example 1 and 687.9 g of water were charged in a 1-L round bottom flask, the mixture was warmed to 73° C. and stirred for 8 hours. After cooling the reaction mixture to 30° C., the aqueous layer was separated and removed to obtain 136.2 g of a yellow solution. The solution was analyzed by a gas chromatography and found to contain 121.0 g of 1,1-dichloro-2-nitroethene. Yield 90.4% (1,1,1-trichloro-2-nitroethane standard)

Example 1

Synthesis of (1E)-N-[(6-chloro-3-pyridinyl)methyl]-N-ethyl-N'-methyl-2-nitro-1,1-ethenediamine (first batch)

352.0 g of n-butyl acetate and 102.9 g of a 35% potassium carbonate aqueous solution were charged in a 1-L separable flask. The solution was cooled to 4° C., 48.8 g of 1,1-dichloro-2-nitroethene (net weight 40.6 g) was added dropwise while stirring over 30 minutes, and 44.8 g of 2-chloro-5-(ethylaminomethyl)pyridine (net weight 44.4 g) was subsequently added dropwise over 3 hours. The reaction mixture was stirred at −4° C. for 15 minutes, 60.6 g of a 40% methyl amine solution was added dropwise over 3 hours, and the stirring was further continued for 4 hours.

The obtained reaction mixture was warmed to 15° C. and extracted four times with 51.5 g, 40.3 g, 30.0 g, and 30.0 g of water, and the obtained four extracted aqueous layers were combined. The combined aqueous layer was extracted four times with 75.0 g of 5-ethyl-2-methylpyridine at 15° C., and the obtained four extracted 5-ethyl-2-methylpyridine layers were combined (amount of the recovered aqueous layer 1, 247.8 g). After washing the combined 5-ethyl-2-methylpyridine layer with 50.0 g of a saturated sodium sulfate solution (amount of the recovered aqueous layer 2, 66.0 g), 800 g of n-heptane was added thereto and concentrated at 4.5 kPa, 25 to 35° C. until the amount of the residual solution was 345 g. 20.0 g of 5-ethyl-2-methylpyridine was added to the concentrated mass, and the mixture was maintained at 40° C. for 1 hour followed by filtration to remove insoluble matters.

The obtained filtrate was flushed down with 10.0 g of 5-ethyl-2-methylpyridine to a 500-ml separable flask, the temperature was adjusted to 35° C. Then 0.01 g of seed crystals of (1E)-N-[(6-chloro-3-pyridinyl)methyl]-N-ethyl-N'-methyl-2-nitro-1,1-ethenediamine was added and the mixture was cooled to 15° C. over 5 hours, and subsequently cooled at −10° C. over 10 hours for crystallization. The crystalline mass was further stirred at −10° C. for 3 hours and filtered (recovered filtrate amount, 304.1 g). The obtained crystals were washed with 300.0 g of n-butyl acetate which had been cooled to −10° C. (recovered washing amount, 305.9 g). The washed crystals were dried at 2.7 kPa, 40° C. for 4 hours to obtain 45.3 g of (1E)-N-[(6-chloro-3-pyridinyl)methyl]-N-ethyl-N'-methyl-2-nitro-1,1-ethenediamine at a content of 98.9%.

Recovery of (1E)-N-[(6-chloro-3-pyridinyl)methyl]-N-ethyl-N'-methyl-2-nitro-1,1-ethenediamine 247.8 g of the recovered aqueous layer 1 was extracted twice with 75.0 g of 5-ethyl-2-methylpyridine to obtain 86.7 g and 85.7 g of the extracted 5-ethyl-2-methylpyridine layers 1 and 2, respectively. 66.0 g of the recovered aqueous layer 2 was extracted with 75.0 g of 5-ethyl-2-methylpyridine to obtain 84.0 g of the extracted 5-ethyl-2-methylpyridine layer 3. 302.8 g of the recovered washing was extracted three times with 51.0 g, 40.0 g and 30.0 g of water to obtain 47.3 g, 41.0 g and 30.5 g of the extracted aqueous layers 1, 2 and 3, respectively.

Example 2

Synthesis of (1E)-N-[(6-chloro-3-pyridinyl)methyl]-N-ethyl-N'-methyl-2-nitro-1,1-ethenediamine (second batch)

351.9 g of n-butyl acetate and 102.7 g of a 35% potassium carbonate aqueous solution were charged in a 1-L separable flask. The solution was cooled to −4° C., 48.8 g of 1,1-dichloro-2-nitroethene (net weight 40.6 g) was added dropwise while stirring over 30 minutes, and 44.8 g of 2-chloro-5-(ethylaminomethyl)pyridine (net weight 44.4 g) was subsequently added dropwise over 3 hours. The reaction mixture was stirred at −4° C. for 15 minutes, 60.6 g of a 40% methyl amine solution was then added dropwise over 3 hours, and stirring was further continued for 4 hours.

The obtained reaction mixture was warmed to 15° C. and extracted four times with the extracted aqueous layers 1, 2 and 3 obtained in Example 1 (46.0 g, 39.8 g, and 30.0 g, respectively) and 30.0 g of water, and the obtained four extracted aqueous layers were combined. The combined aqueous layer was extracted at 15° C. four times with the extracted 5-ethyl-2-methylpyridine layers 1, 2 and 3 obtained in Example 1 (84.5 g, 83.9 g and 82.4 g, respectively) and 75.0 g of 5-ethyl-2-methylpyridine, and the obtained four extracted 5-ethyl-2-methylpyridine layers were combined (amount of the recovered aqueous layer 1, 269.8 g). After washing the combined 5-ethyl-2-methylpyridine layer with 50.0 g of saturated sodium sulfate solution (amount of the recovered aqueous layer 2, 72.4 g), 800 g of n-heptane was added thereto and the mixture was concentrated at 4.5 kPa, 25 to 35° C. until the amount of the residual solution was 321 g. 51.2 g of 5-ethyl-2-methylpyridine was added to the concentrated mass and the mixture was maintained at 40° C. for 1 hour followed by filtration to remove insoluble matters.

The obtained filtrate was flushed down with 10.0 g of 5-ethyl-2-methylpyridine to a 500-ml separable flask, the temperature was adjusted to 35° C., and then 20.0 g of n-heptane was added dropwise over minutes. 0.01 g of seed crystals of (1E)-N-[(6-chloro-3-pyridinyl)methyl]-N-ethyl-N'-methyl-2-nitro-1,1-ethenediamine was added to the mass and the mixture was cooled to 15° C. over 5 hours, and subsequently cooled to −10° C. over 10 hours for crystallization. The crystalline mass was further stirred at −10° C. for 3 hours and filtered (recovered filtrate amount, 332.06 g). The obtained crystals were washed with 60.0 g of 5-ethyl-2-methylpyridine/n-heptane (9/1 weight ratio) which had been cooled to −10° C., and subsequently washed with 200.0 g of n-heptane which had been cooled to −10° C. (recovered washing amount, 264.87 g). The washed crystals were dried at 2.7 kPa, 40° C. for 4 hours to obtain 53.54 g of (1E)-N-[(6-chloro-3- pyridinyl)methyl]-N-ethyl-N'-methyl-2-nitro-1,1-ethenediamine with a content of 99.0%.

Recovery of (1E)-N-[(6-chloro-3-pyridinyl)methyl]-N-ethyl-N'-methyl-2-nitro-1,1-ethenediamine 269.8 g of the recovered aqueous layer 1 was extracted twice with 75.0 g of 5-ethyl-2-methylpyridine to obtain 87.6 g and 87.6 g of the extracted 5-ethyl-2-methylpyridine layers 1 and 2, respectively. 72.4 g of the recovered aqueous layer 2 was extracted with 75.0 g of 5-ethyl-2-methylpyridine to obtain 87.3 g of the extracted 5-ethyl-2-methylpyridine layer 3. 328.6 g of the recovered filtrate and 260.5 g of recovered washing were mixed, and then extracted three times with 71.3 g, 40.1 g and 30.1 g of water to obtain 52.0 g, 46.7 g and 33.4 g of the extracted aqueous layers 1, 2 and 3, respectively.

Example 3

Synthesis of (1E)-N-[(6-chloro-3-pyridinyl)methyl]-N-ethyl-N'-methyl-2-nitro-1,1-ethenediamine (third batch)

351.9 g of n-butyl acetate and 102.7 g of a 35% potassium carbonate aqueous solution were charged in a 1-L separable flask. The solution was cooled to −4° C., 48.8 g of 1,1-dichloro-2-nitroethene (net weight 40.6 g) was added dropwise while stirring over 30 minutes, and 44.8 g of 2-chloro-5-(ethylaminomethyl)pyridine (net weight 44.4 g) was subsequently added dropwise over 3 hours. The reaction mixture was stirred at −4° C. for 15 minutes, 60.6 g of a 40% methyl amine aqueous solution was added dropwise over 3 hours, and stirring was further continued for 4 hours.

The obtained reaction mixture was warmed to 15° C. and extracted four times with the extracted aqueous layers 1, 2 and 3 obtained in Example 2 (50.3 g, 45.2 g, and 31.9 g, respectively) and 30.0 g of water, and the obtained four extracted aqueous layers were combined. The combined aqueous layer obtained was extracted at 15° C. four times with the extracted 5-ethyl-2-methylpyridine layers 1, 2 and 3 obtained in Example 2 (85.5 g, 85.6 g and 90.4 g, respectively) and 75.0 g of 5-ethyl-2-methylpyridine, and the obtained four extracted 5-ethyl-2-methylpyridine layers were combined. After washing the combined 5-ethyl-2-methylpyridine layer with 50.0 g of saturated sodium sulfate solution, 800 g of n-heptane was added thereto and the mixture was concentrated at 4.5 kPa, 25 to 35° C. until the amount of the residual solution was 350.6 g. 20.0 g of 5-ethyl-2-methylpyridine was added to the concentrated mass, and the mixture was maintained at 40° C. for 1 hour followed by filtration to remove insoluble matters.

The obtained filtrate was flushed down with 10.0 g of 5-ethyl-2-methylpyridine to a 500 ml separable flask, the temperature was adjusted to 35° C., and then 20.0 g of n-heptane was added dropwise over minutes. 0.01 g of seed crystals of (1E)-N-[(6-chloro-3-pyridinyl)methyl]-N-ethyl-N'-methyl-2-nitro-1,1-ethenediamine was added to the mass and the mixture was cooled to 15° C. over 5 hours, and subsequently cooled to −10° C. over 10 hours for crystallization. The crystalline mass was further stirred at −10° C. for 3 hours and filtered. The obtained crystals were washed with 60.0 g of 5-ethyl-2-methylpyridine/n-heptane (9/1 weight ratio) which had been cooled to −10° C., and subsequently washed with 200.0 g of n-heptane cooled to −10° C. The washed crystals were dried at 2.7 kPa, 40° C. for 4 hours to obtain 61.4 g of (1E)-N-[(6-chloro-3-pyridinyl)methyl]-N-ethyl-N'-methyl-2-nitro-1,1-ethenediamine with a content of 99.2%.

Industrial Applicability

According to the production method of the present invention, the α-unsaturated amine compound represented by Formula (1) effective as an active ingredient of an insecticide can be separated and purified by a method which does not require a chlorinated organic solvent and is yet suitable for industrial-scale production.

The invention claimed is:
1. A method for purifying an α-unsaturated amine compound represented by Formula (1), comprising a step of extracting with water the compound of Formula (1) from a crude product of the α-unsaturated amine compound represented by Formula (1), and a step of extracting with 5 ethyl-2-methylpyridine the α-unsaturated amine compound of Formula (1) from the aqueous solution containing the compound of Formula (1) obtained in the previous step to obtain a 5-ethyl-2-methylpyridine solution of the compound of Formula (1):

[Chemical Formula 1]

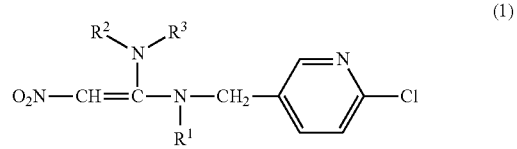

(1)

wherein $R^1$ represents a hydrogen atom, a $C_{1-4}$ alkyl group, a halo $C_{1-4}$ alkyl group, a $C_{1-4}$ alkoxy-$C_{1-4}$ alkyl group, a $C_{7-9}$ aralkyl group, or an optionally substituted phenyl group, $R^2$ represents a hydrogen atom, a $C_{1-4}$ alkyl group, or a $C_{7-9}$ aralkyl group, and $R^3$ represents a hydrogen atom, a $C_{1-5}$ alkyl group, a halo $C_{1-4}$ alkyl group, a hydroxy $C_{1-4}$ alkyl group, a $C_{1-4}$ alkoxy-$C_{1-4}$ alkyl group, $C_{2-4}$ alkenyl group, or a $C_{7-9}$ aralkyl group.

2. The method according to claim 1 further comprising a step of isolating an α-unsaturated amine compound of Formula (1) in the form of crystal from the 5-ethyl -2-methylpyridine solution of the compound of Formula (1).

3. The method according claim 1, wherein the crude product of the α-unsaturated amine compound of Formula (1) is a crude product obtained by reacting 1,1-dichloro-2-nitroethene represented by Formula (2)

[Chemical Formula 2]

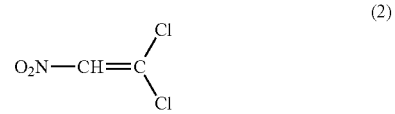

(2)

with a pyridyl methyl amine compound represented by Formula (3)

[Chemical Formula 3]

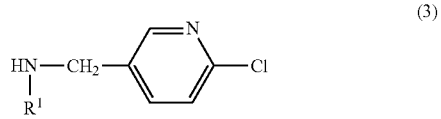

(3)

wherein R¹ is as defined above, and subsequently reacting the obtained product with an amine compound represented by Formula (4)

[Chemical Formula 4]

(4)

wherein R² and R³ are as defined above; or reacting 1,1-dichloro-2-nitroethene of Formula (2) with the amine compound of Formula (4), and subsequently reacting the obtained product with the pyridyl methyl amine compound of Formula (3).

4. The method according to claim 1, wherein R¹ and R² are $C_{1-4}$ alkyl groups, and R³ is a hydrogen atom.

* * * * *